US00PP10415P

United States Patent [19]

Jessel, Jr.

[11] Patent Number: Plant 10,415

[45] Date of Patent: May 26, 1998

[54] CARNATION PLANT NAMED 'CFPC DREAM'

[75] Inventor: Walter H. Jessel, Jr., Gonzales, Calif.

[73] Assignee: California Florida Plant Co., L.P., Salinas, Calif.

[21] Appl. No.: 749,920

[22] Filed: Nov. 12, 1996

[51] Int. Cl.[6] ..... A01H 5/00

[52] U.S. Cl. ..... Plt./70.2

[58] Field of Search ..... Plt./70.2

*Primary Examiner*—Howard J. Locker

*Attorney, Agent, or Firm*—Christie, Parker & Hale, LLP

[57] ABSTRACT

A new plant variety of carnation pot plant producing violet pictoee and striped flowers.

1 Drawing Sheet

BACKGROUND OF THE INVENTION

The present invention relates to a new and distinct variety of carnation plant which was discovered as a sport in a controlled planting of the cultivar 'CFPC Pageant'. The varietal denomination of this new carnation is 'CFPC Dream'. The variety 'CFPC Pageant' was the original name for the variety 'CFPC Whisper ' disclosed in U.S. Plant Pat. Application Ser. No. 08/749922. The original mutation discovered was two stems of the parent plant.

SUMMARY OF THE INVENTION

The new variety is a true dwarf carnation suitable for growing in 4 to 4½-inch pots (1 plant, 1 pinch, i.e. one cutting or plant per pot and one pinch of the terminal portion to induce lateral shoots), tolerant to temperatures of about 10° to 120° F., with a keeping quality of about 3 to 4 weeks for substantially all blooms on the plant. Flower buds open from green bud to maturity with moderate light. No disease problems have been observed as yet.

If planted outdoors, the new variety will continue to recycle growth and blooms. It appears to be perennial in nature in most sections of the country.

In addition to the foregoing, the new variety exhibits superior resistance to soil borne diseases such as *F. oxysporum*, strains 1 and 2, and *F. graminearum*, and root-rots such as damping off, water molds, and the like.

Asexual reproduction by propagation by side shoot cuttings of the new variety as performed in Salinas, Calif., shows that the foregoing and other distinguishing characteristics come true to form and are established and transmitted through succeeding propagations.

'CFPC Dream' has flowers with a lavender background color, whereas 'CFPC Pageant' has flowers with a white background.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Phenotypic expression and color descriptions may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Dream'.

Classification:

*Botanical.*—*Dianthus caryophyllus.*

*Commercial.*—Carnation, Greenhouse type as a pot variety producing flower sprays.

Parentage: Sport of 'CFPC Pageant'.

1. Plant:
   - *Height.*—Pinched plants are about 7 to 9 inches.
   - *Growing habit.*—Herbaceous, semi-upright.
   - *Blooming habit.*—As a pot spray.
   - *Blooming season.*—Year round.
   - *Rooting time.*—About 17 days.
   - *Mutation prone.*—No.
   - *Disease resistance.*—Good.
   - *Temperature tolerance.*—Wide range.
   - *Breaking action.*—Excellent, approximately 8 lateral shoots which bud flower per plant.
2. Foliage:
   - *Color.*—Upper side: Near 138A. Lower side: Near 139B.
   - *Size.*—About 4 inches long, about ¼ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Near 137A.
3. Bud:
   - *Shape.*—Ovoid.
   - *Color.*—Near 137B.
   - *Length.*—About 1 inch.
   - *Diameter.*—About ⅜ inch.
4. Calyx:
   - *Number of sepal.*—About 5.
   - *Length.*—About ½ inch.
   - *Width.*—About 3/16 inch.
   - *Color.*—Outside — Near 144A. Inside — Near 143C.
5. Bloom:
   - *Shape.*—Round.

*Size.*—Diameter average: About 1¾ inches. Depth average: About ⅞ inch.

*Borne.*—As a spray, approximately 6 to 8 blooms per flowering stem, flowering stem length is about 7.5 to 8.5 inches.

*Color.*—General tonality: Violet picotee and striped purple, darker red-purple coloration on all petals, lighter than 69C. Upper side: Near 69C to 73D. Lower side: Lighter than upper side. Center: Near 69C. Outer petals: Near 71C picotee edge and stripes.

*Keeping quality.*—About 3 weeks, flower petals dry and shrivel and do not fall from plant.

*Fragrance.*—None.

6. Petals:

*Number.*—About 20.

*Outer petals.*—Lengths: About 1½ inches. Width: About ¾ inch.

*Central petals.*—Length: About 1⅜ inches. Width: About ½ inch.

*Texture.*—Smooth.

*Form.*—Fan shaped.

*Appearance.*—Shiny, petal margins are smooth.

7. Reproductive Organs

Stamens.—None (male sterile)

*Pistils.*—Number: About 1. Color: Whiter than 155D. Length: About 1 inch.

*Stigma.*—Number: About 2 or 3. Color: Whiter than 155D.

*Ovary.*—Shape: Conical. Color: Base — near 154C. Body — near 145B. Apex — Near 19D.

*Fertility.*—Female: Good. Male: Sterile.

I claim:

1. A new and distinct variety of carnation plant substantially as shown and described.

* * * * *

PLT-273 SR
C5203 OR PP 010,415
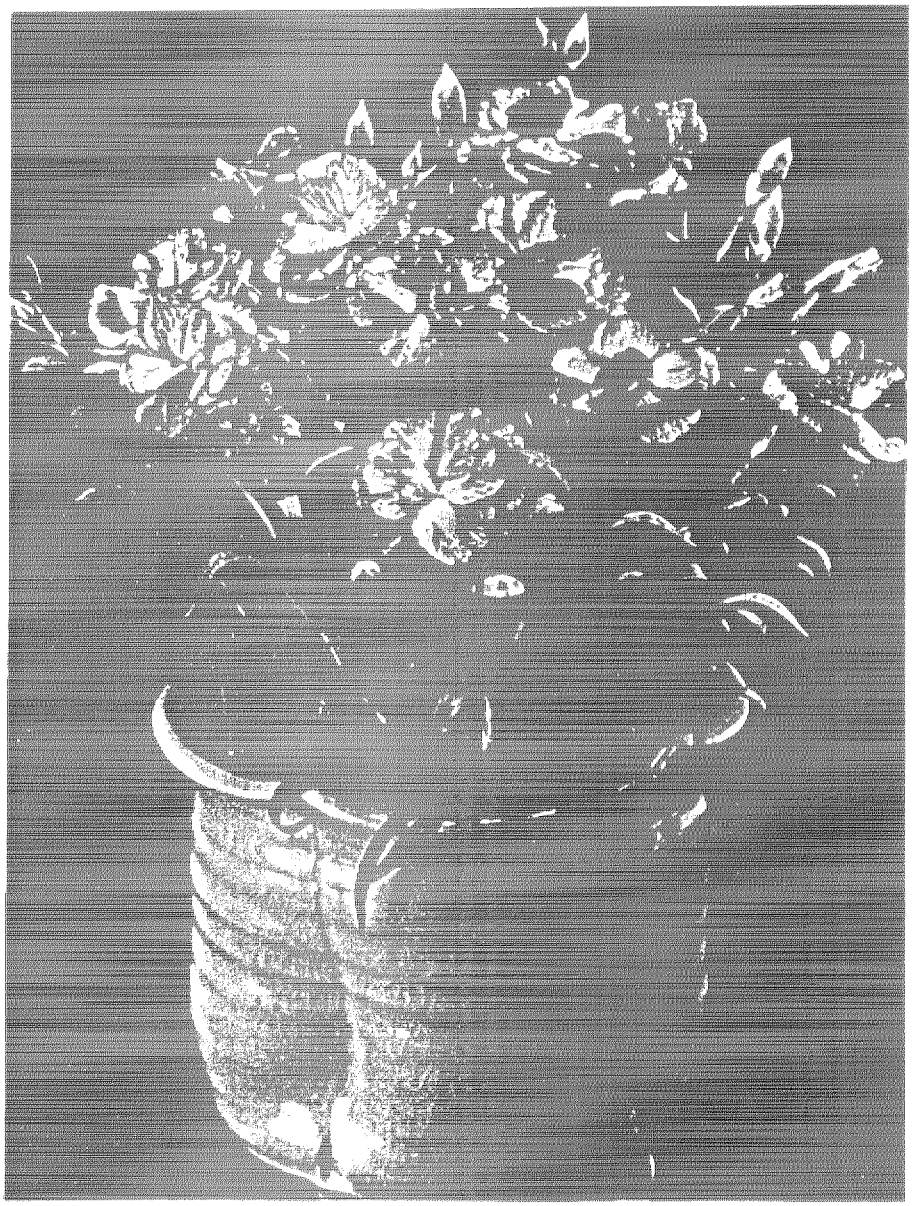

UNITED STATES PATENT AND TRADEMARK OFFICE

CERTIFICATE OF CORRECTION

PATENT NO. : Plant 10,415
DATED : May 26, 1998
INVENTOR(S) : Walter H. Jessel, Jr.

It is certified that error appears in the above-indentified patent and that said Letters Patent is hereby corrected as shown below:

Column 2, line 28, after "bud" insert -- and -- .
Column 2, line 45, change "sepal" to -- sepals -- .

Signed and Sealed this

Third Day of August, 1999

*Attest:*

Q. TODD DICKINSON

*Attesting Officer*

*Acting Commissioner of Patents and Trademarks*